US012797321B2

(12) United States Patent
Song et al.

(10) Patent No.: US 12,797,321 B2
(45) Date of Patent: Nov. 17, 2026

(54) COSMETIC COMPOSITION COMPRISING EUTECTIC MIXTURE OF VITAMIN C

(71) Applicant: LG HOUSEHOLD & HEALTH CARE LTD., Seoul (KR)

(72) Inventors: Ji Eun Song, Seoul (KR); Seung Hyun Jun, Seoul (KR); Hyun Min Hwang, Seoul (KR); Mun Ju Shin, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 200 days.

(21) Appl. No.: 18/696,821

(22) PCT Filed: Sep. 28, 2022

(86) PCT No.: PCT/KR2022/014560

§ 371 (c)(1),
(2) Date: Mar. 28, 2024

(87) PCT Pub. No.: WO2023/055074

PCT Pub. Date: Apr. 6, 2023

(65) Prior Publication Data

US 2024/0390254 A1 Nov. 28, 2024

(30) Foreign Application Priority Data

Sep. 29, 2021 (KR) ........................ 10-2021-0129132
Aug. 11, 2022 (KR) ........................ 10-2022-0100392

(51) Int. Cl.

| | |
|---|---|
| ***A61K 8/67*** | (2006.01) |
| ***A61K 8/02*** | (2006.01) |
| ***A61K 8/44*** | (2006.01) |
| ***A61Q 19/02*** | (2006.01) |
| ***A61Q 19/08*** | (2006.01) |

(52) U.S. Cl.
CPC ............ *A61K 8/676* (2013.01); *A61K 8/0216* (2013.01); *A61K 8/44* (2013.01); *A61Q 19/02* (2013.01); *A61Q 19/08* (2013.01)

(58) Field of Classification Search
None
See application file for complete search history.

(56) References Cited

FOREIGN PATENT DOCUMENTS

| | | | | | |
|---|---|---|---|---|---|
| CN | 1856294 | A | | 11/2006 | |
| CN | 112107880 | A | | 12/2020 | |
| EP | 4011353 | A1 | * | 6/2022 | ............. A61Q 19/00 |
| KR | 10-2018-0016352 | A | | 2/2018 | |
| KR | 10-2021-0075949 | A | | 6/2021 | |
| KR | 10-2278980 | B1 | | 7/2021 | |
| WO | WO 2021/119664 | A1 | | 6/2021 | |

OTHER PUBLICATIONS

International Search Report, issued in PCT/KR2022/014560, PCT/ISA/210, dated Dec. 15, 2022.

* cited by examiner

*Primary Examiner* — H. Sarah Park
(74) *Attorney, Agent, or Firm* — Birch, Stewart, Kolasch & Birch, LLP

(57) ABSTRACT

The present invention relates to a cosmetic compound comprising a eutectic mixture containing vitamin C and betaine and a preparation method therefor and can provide a cosmetic composition that contains vitamin C in the form of a eutectic mixture and thus exhibits high solubility in various types of solvents, excellent oxidation stability, and high skin permeability.

8 Claims, 6 Drawing Sheets

<FIG.1>
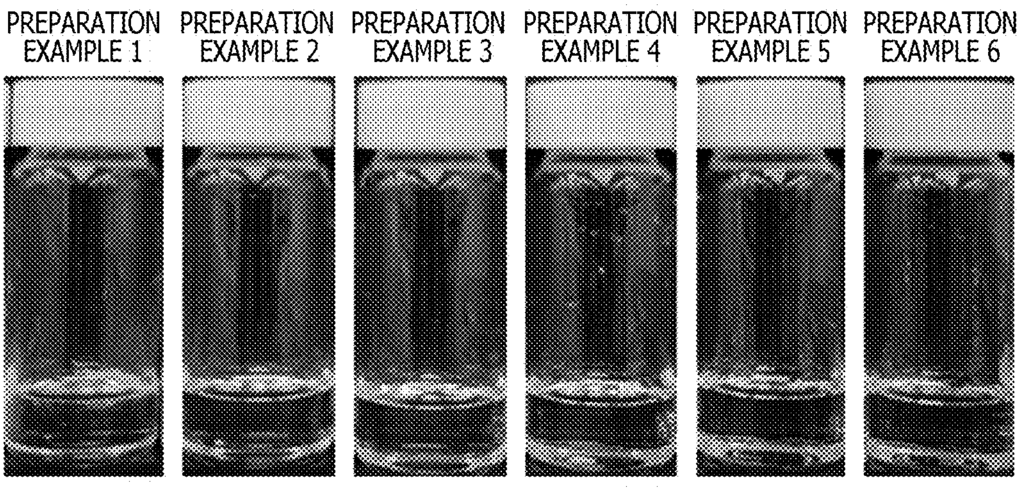
<FIG.2>
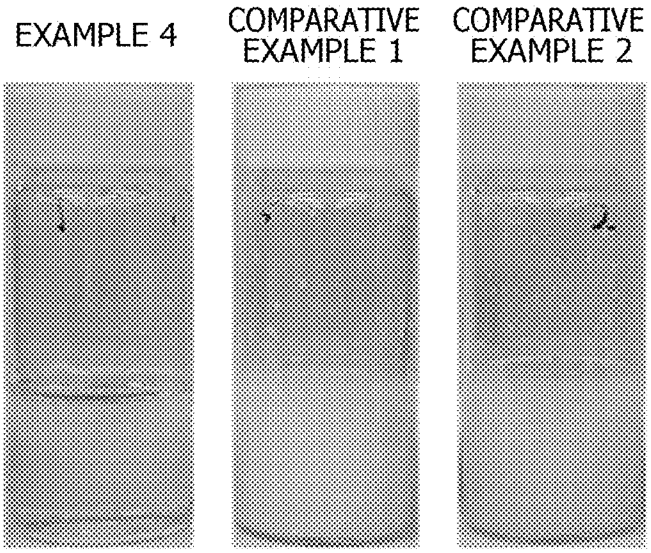

<FIG.3>
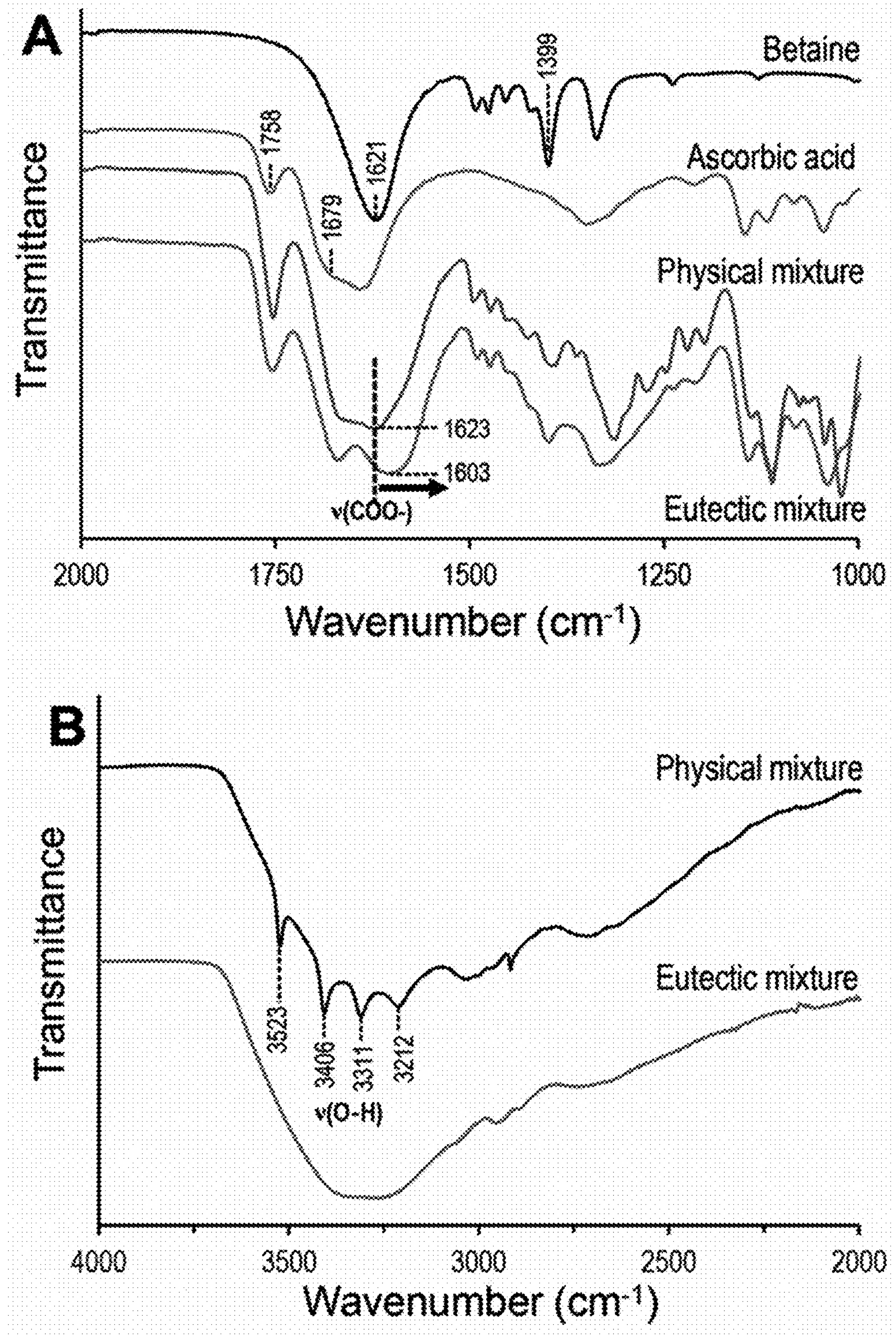

<FIG.5>
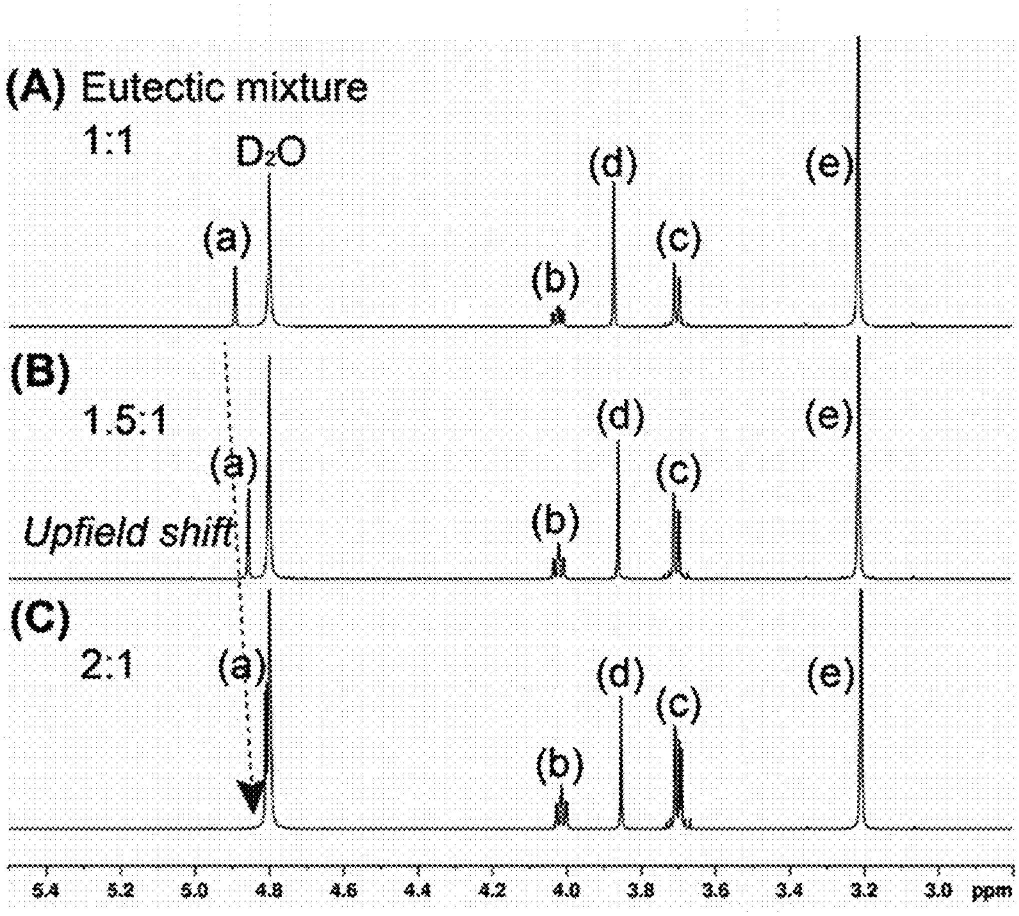

<FIG.6A>
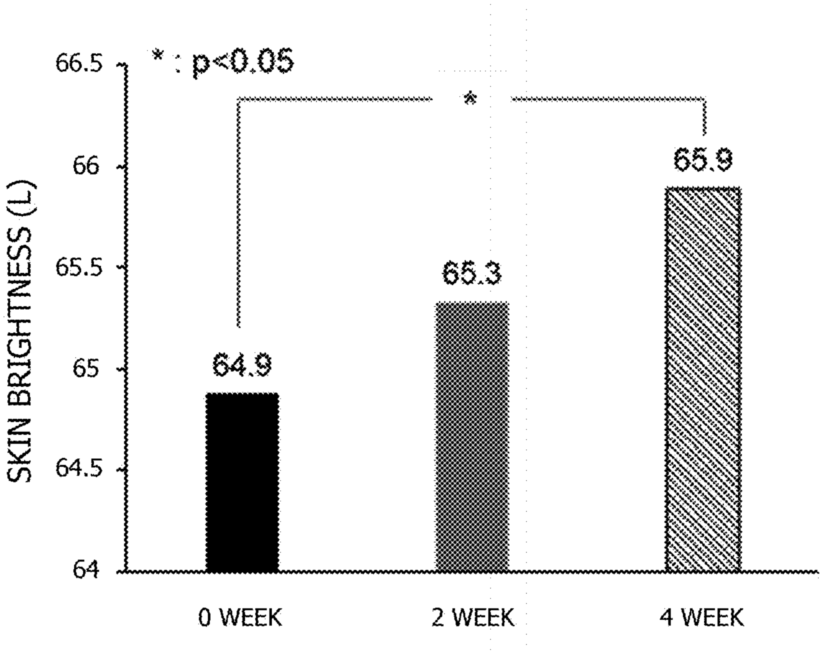
<FIG.6B>
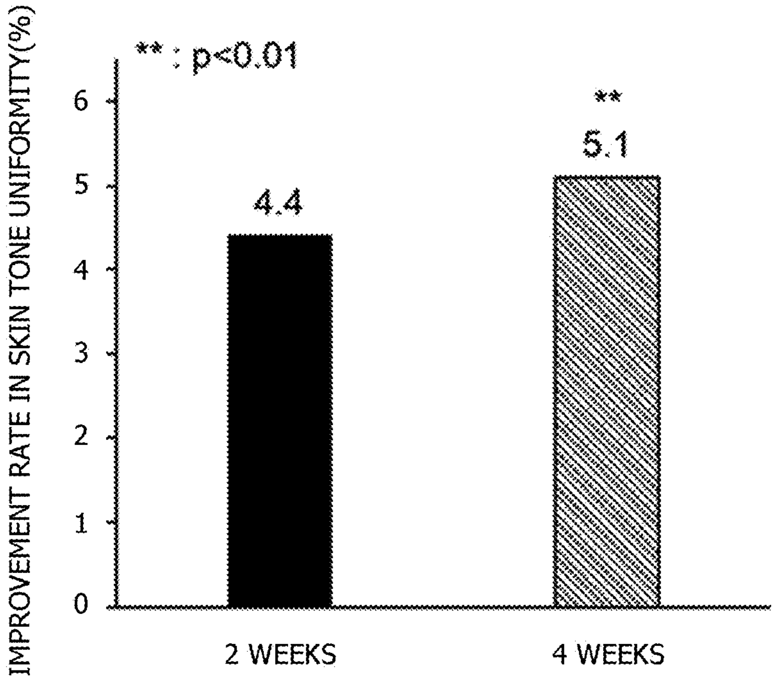

<FIG.7>
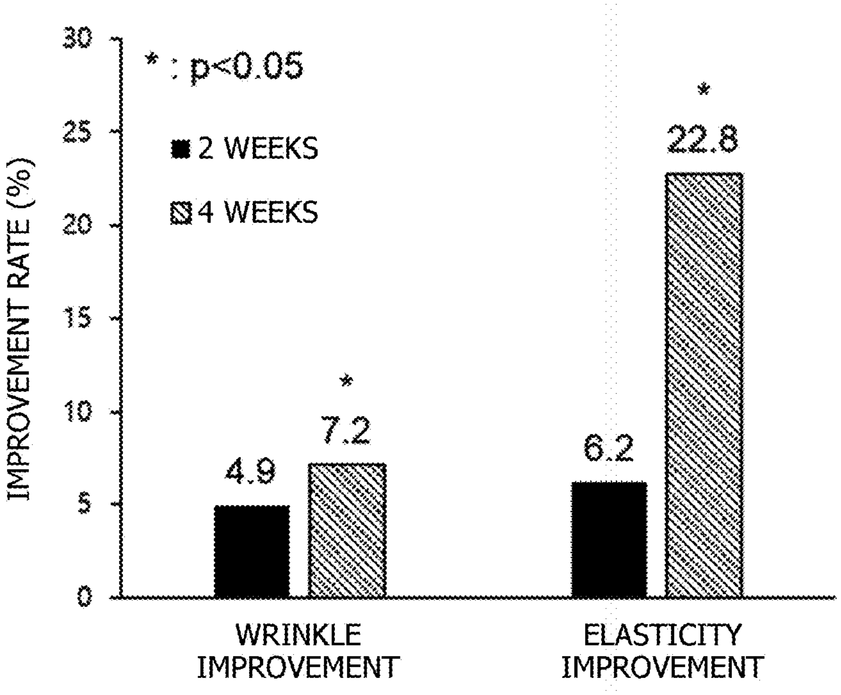

COSMETIC COMPOSITION COMPRISING EUTECTIC MIXTURE OF VITAMIN C

TECHNICAL FIELD

The present invention relates to a cosmetic composition comprising a eutectic mixture containing vitamin C and a method of preparing the same.

BACKGROUND ART

Melanin, which determines a person's skin color, is produced in melanocytes present in the basal layer of the skin and transferred to surrounding keratinocytes to give the skin its color. In particular, overproduction of melanin causes pigmentation, resulting in freckles and blemishes. Vitamin C, which is known as a representative component for skin brightening, not only reduces pigmentation by suppressing the production of melanin, but also slows down skin aging by reducing reactive oxygen species caused by the external environment and helps collagen synthesis to improve skin wrinkles and skin elasticity.

Although vitamin C can be dissolved in water in a relatively large amount, it is easily decomposed due to rapid oxidation. Oxidation stability can be improved in a non-aqueous solvent, but the solubility of vitamin C is extremely low in the non-aqueous solvent. Since it is difficult for vitamin C, which is hydrophilic, to permeate the stratum corneum, the outermost layer of the skin, a large amount of vitamin C is required to induce sufficient bioactivity. For this reason, in the pharmaceutical and cosmetic fields, water-based vitamin C formulations are mainly provided with a very short shelf-life, and when vitamin C was stored at low temperatures to delay oxidative decomposition, the precipitation of vitamin C caused quality issues and inconvenience to users.

There has been a lot of effort and research to improve the solubility and instability of vitamin C. As a specific example, in Patent Documents 1 and 2, a glycol-type solvent with three carbon atoms and a precipitation prevention agent were used to delay the oxidation of vitamin C and prevent precipitation at low temperatures by reducing the amount of water in the formulation. In Patent Document 3, a method of improving stability by dispersing vitamin C powder in silicone-based oil was examined. In these patents, although the stability of vitamin C was partially improved, solvent selectivity was limited, skin absorption was not improved, and vitamin C was precipitated at high contents above a certain level. In addition, vitamin C dispersed in silicone-based oil is dispersed in the form of fine particles rather than in solution, which is not suitable for transdermal delivery and could cause irritation.

RELATED-ART DOCUMENTS

Patent Documents (Patent Document 1) JP WO2019-131892 A1
(Patent Document 2) JP WO2019-189742 A1
(Patent Document 3) U.S. Pat. No. 10,912,729 B2

DISCLOSURE

Technical Problem

The present inventors completed the present invention after confirming that when vitamin C and betaine are prepared in the form of a eutectic mixture, the solubility in various aqueous and non-aqueous solvents increases significantly, vitamin C remains stable without being precipitated even at a low temperature, and the skin permeability of vitamin C is improved.

An object of the present invention is to provide a cosmetic composition and a quasi-drug composition that have high solubility in various solvent conditions, excellent oxidation stability, and excellent skin permeability by including vitamin C and betaine in the form of a eutectic mixture in the cosmetic composition.

Technical Solution

In order to solve the above problems, the present invention provides a cosmetic composition comprising a eutectic mixture containing vitamin C and betaine.

The present invention also provides a method of preparing a cosmetic composition, which comprises: preparing a eutectic mixture by mixing vitamin C and betaine; and adding the eutectic mixture to prepare a cosmetic composition.

The present invention also provides a quasi-drug composition comprising a eutectic mixture containing vitamin C and betaine.

The present invention also provides a method of preparing a quasi-drug composition, which comprises: preparing a eutectic mixture by mixing vitamin C and betaine; and adding the eutectic mixture to prepare a quasi-drug composition.

Advantageous Effects

The present invention can provide a cosmetic composition and a quasi-drug composition which includes vitamin C and betaine in the form of a eutectic mixture, thus have significantly improved vitamin C solubility in various aqueous and non-aqueous solvents, and excellent vitamin C oxidation stability, even when a large amount of vitamin C is included. In addition, the present invention can provide a composition, which is stable even at a low temperature without precipitation of vitamin C, exhibits high skin permeability of vitamin C, and has an effect of improving skin brightening, skin tone uniformity, wrinkles, and elasticity.

DESCRIPTION OF DRAWINGS

FIG. 1 shows the results of whether a eutectic mixture composed of ascorbic acid and betaine is formed at various molar ratios of ascorbic acid and betaine according to Experimental Example 1.

FIG. 2 shows the result of comparing vitamin C, a simple mixture of vitamin C and betaine, and a eutectic mixture of vitamin C and betaine to see whether they are stable without being precipitated in a composition, which includes a large amount of non-aqueous solvent, according to Experimental Example 2.

FIG. 3 shows the results of infrared spectrum analysis of vitamin C (ascorbic acid), betaine, a simple mixture of vitamin C and betaine, and a eutectic mixture of vitamin C and betaine, according to Experimental Example 5.

FIG. 5 shows the $^{1}H$ NMR analysis result of a eutectic mixture of vitamin C and betaine according to Experimental Example 5.

FIG. 6 shows the graphs of the skin brightness and skin uniformity improvement rates of a eutectic mixture including vitamin C, according to Experimental Example 6.

FIG. 7 shows the graph of the wrinkle and elasticity improvement rates of a eutectic mixture including vitamin C according to Experimental Example 6.

MODES OF THE INVENTION

Figure 4A:
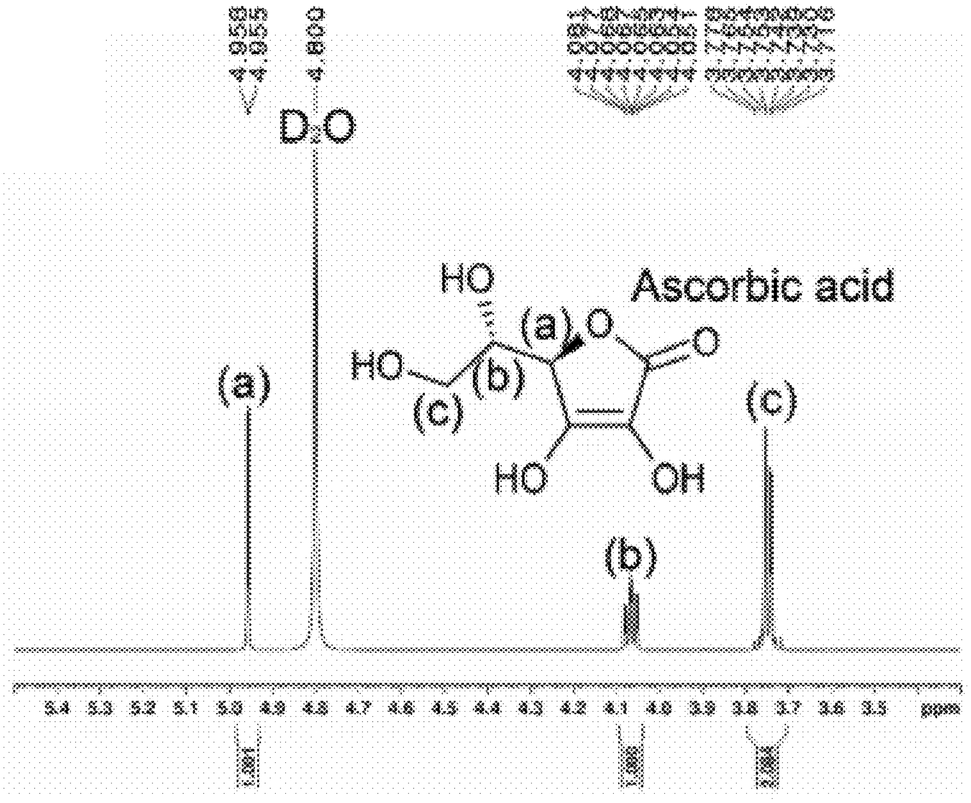
FIG. 4A shows the $^{1}H$ NMR analysis result of vitamin C.

Hereinafter, the present invention will be described in detail.

As the present invention is subject to various changes and can have various forms, specific embodiments will be illustrated and described in detail below. However, it is not intended to limit the present invention to a specific disclosed form, and it should be understood to include all changes, equivalents, and substitutes in the spirit and technical scope of the present invention.

The present invention provides a cosmetic composition comprising a eutectic mixture, which comprises vitamin C and betaine.

As in the present invention, when vitamin C and betaine form a eutectic mixture, the melting point can become much lower than their respective melting points due to hydrogen bonding. The present inventors confirmed that the eutectic mixture has significantly high solubility not only in an aqueous solvent, but also in various non-aqueous solvents or aqueous/non-aqueous mixed solvents, and it can maintain a stable composition in various conditions and can be utilized to allow large amounts of vitamin C to permeate the skin due to its good skin permeability.

In the present invention, "vitamin C" is also called L-ascorbic acid or ascorbic acid and has the chemical structure below.

[Chemical Formula 1]

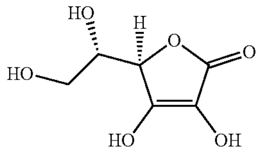

In the present invention, "betaine (trimethylglycine)," which forms a eutectic mixture with vitamin C, is an amino acid derivative extracted from sugar beets and has moisturizing, soothing, anti-inflammatory effects and has the chemical structure below.

[Chemical Formula 2]

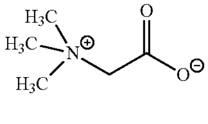

In the present invention, a eutectic mixture may be prepared from vitamin C and betaine and preferably prepared from vitamin C, betaine, and water.

In the present invention, the molar ratio of vitamin C and betaine forming the eutectic mixture may be 1:0.1 to 1:10 but is not limited thereto. Specifically, the molar ratio of vitamin C and betaine may be 1:0.1 to 1:9, 1:0.1 to 1:8, 1:0.1 to 1:7, 1:0.1 to 1:6, 1:0.2 to 1:10, 1:0.2 to 1:9, 1:0.2 to 1:8, 1:0.2 to 1:7, 1:0.2 to 1:6, 1:0.25 to 1:10, 1:0.25 to 1:9, 1:0.25 to 1:8, 1:0.25 to 1:7, 1:0.25 to 1:6, 1:0.3 to 1:10, 1:0.3 to 1:9, 1:0.3 to 1:8, 1:0.3 to 1:7, or 1:0.3 to 1:6, and preferably, the molar ratio of vitamin C and betaine may be 1:0.3 to 1:6. When the molar ratio of vitamin C and betaine is outside the above range, it may be difficult to prepare a eutectic mixture.

In the present invention, when a eutectic mixture of vitamin C and betaine is prepared, the most suitable ratio for preparing a eutectic mixture with high solubility and stability may be derived considering the type and number of functional groups and the electric charge of each component.

In the present invention, the content of vitamin C in the eutectic mixture may be 6 parts by weight or more, 10 parts by weight or more, 11 parts by weight or more, 13 parts by weight or more, 18 parts by weight or more, 19 parts by weight or more, or 23 parts by weight or more, or 94 parts by weight or less, 86 parts by weight or less, 81 parts by weight or less, 79 parts by weight or less, 76 parts by weight or less, 74 parts by weight or less, 70 parts by weight or less, 68 parts by weight or less, 64 parts by weight or less, 47 parts by weight or less, 43 parts by weight or less, or 40 parts by weight or less, based on 100 parts by weight of the total eutectic mixture.

More specifically, the content of vitamin C in the eutectic mixture may be 13 to 94 parts by weight, 13 to 86 parts by weight, 13 to 79 parts by weight, 23 to 94 parts by weight, 23 to 86 parts by weight, 23 to 79 parts by weight, 11 to 81 parts by weight, 11 to 74 parts by weight, 11 to 68 parts by weight, 19 to 81 parts by weight, 19 to 74 parts by weight, 19 to 68 parts by weight, 10 to 76 parts by weight, 10 to 70 parts by weight, 10 to 64 parts by weight, 18 to 76 parts by weight, 18 to 70 parts by weight, 18 to 64 parts by weight, 6 to 47 parts by weight, 6 to 43 parts by weight, 6 to 40 parts by weight, 11 to 47 parts by weight, 11 to 43 parts by weight, or 11 to 40 parts by weight.

In the present invention, the content of betaine in the eutectic mixture may be 3 parts by weight or more, 5 parts by weight or more, 6 parts by weight or more, 7 parts by weight or more, 10 parts by weight or more, 11 parts by weight or more, 12 parts by weight or more, 14 parts by weight or more, 17 parts by weight or more, 18 parts by weight or more, or 21 parts by weight or more, or 87 parts by weight or less, 77 parts by weight or less, 75 parts by weight or less, 71 parts by weight or less, 67 parts by weight or less, 63 parts by weight or less, 44 parts by weight or less, or 39 parts by weight or less, based on 100 parts by weight of the total eutectic mixture.

More specifically, the content of betaine in the eutectic mixture may be 6 to 77 parts by weight, 6 to 87 parts by weight, 14 to 77 parts by weight, 14 to 87 parts by weight, 21 to 77 parts by weight, 21 to 87 parts by weight, 5 to 67 parts by weight, 5 to 75 parts by weight, 12 to 67 parts by weight, 12 to 75 parts by weight, 18 to 67 parts by weight, 18 to 75 parts by weight, 5 to 63 parts by weight, 5 to 71 parts by weight, 11 to 63 parts by weight, 11 to 71 parts by weight, 17 to 63 parts by weight, 17 to 71 parts by weight, 3 to 44 parts by weight, 3 to 39 parts by weight, 7 to 44 parts by weight, 7 to 39 parts by weight, 10 to 44 parts by weight, or 10 to 39 parts by weight.

The eutectic mixture according to the present invention may further comprise water. Due to water, the melting point of the eutectic mixture of vitamin C and betaine may be decreased, the vitamin C in the composition may be stably maintained, and the properties may be uniform and stable even in various conditions without precipitation of vitamin C.

In the present invention, the content of water in the eutectic mixture may be 0.00001 parts by weight to 50 parts by weight, 0.00001 to 40 parts by weight, 0.01 to 30 parts by weight, or 1 to 20 parts by weight, based on 100 parts by weight of the total eutectic mixture, but is not limited thereto. When the water content exceeds the above range, the oxidation stability of vitamin C in the eutectic mixture may decrease.

The cosmetic composition containing the eutectic mixture according to the present invention may be adjusted to a pH of 3.0 to 7.0 in order to improve discomfort such as skin irritation when applied to the skin.

In order to adjust the pH to the above range, the cosmetic composition may additionally comprise a pH adjuster such as potassium hydroxide or tromethamine.

In the present invention, the eutectic mixture may be added to the cosmetic composition at a high content, and it is stably dissolved even when stored at room temperature or kept refrigerated and maintains the efficacy of vitamin C, making it possible to maintain the quality of the product.

In the cosmetic composition comprising a eutectic mixture comprising vitamin C, vitamin C may be included in an amount of 0.00001 parts by weight or more, 0.01 parts by weight or more, 1 part by weight or more, 5 parts by weight or more, 8 parts by weight or more, 10 parts by weight or more, 12 parts by weight or more, 15 parts by weight or more, 18 parts by weight or more, 20 parts by weight or more, or 65 parts by weight or less, 60 parts by weight or less, 55 parts by weight or less, 52 parts by weight or less, 50 parts by weight or less, 48 parts by weight or less, 45 parts by weight or less, 40 parts by weight or less, 35 parts by weight or less, or 33 parts by weight or less, based on 100 parts by weight of the total cosmetic composition, but is not limited thereto.

Specifically, vitamin C may be included in an amount of 0.00001 to 65 parts by weight, 1 to 60 parts by weight, 5 to 55 parts by weight, 5 to 50 parts by weight, 10 to 45 parts by weight, 10 to 40 parts by weight, 15 to 40 parts by weight, 20 to 40 parts by weight, 20 to 35 parts by weight, based on 100 parts by weight of the total cosmetic composition.

The cosmetic composition according to the present invention may include the eutectic mixture in an amount of 0.00001 to 80 parts by weight, for example, 0.001 to 75 parts by weight, 0.1 to 70 parts by weight, or 0.5 to 60 parts by weight, or 0.1 to 50 parts by weight, based on 100 parts by weight of the total cosmetic composition, but is not limited thereto. The content of the eutectic mixture may be appropriately adjusted depending on the formulation of the cosmetic composition.

The cosmetic composition of the present invention may further comprise a solvent in addition to the eutectic mixture. The solvent may be an aqueous solvent, a non-aqueous solvent, or a mixture thereof.

In the present invention, a "non-aqueous solvent" may be a solvent including a solvent other than water. Solvents other than water may be polyhydric alcohols, specifically one or more selected from the group consisting of ethylene glycol, 1,2-propanediol (propylene glycol), 1,3-propanediol, 1,3-butylene glycol, pentylene glycol, hexylene glycol, glycerin, diglycerin, dipropylene glycol, and a mixture thereof, and more specifically may be one or more selected from the group consisting of propanediol, butylene glycol, dipropylene glycol, glycerin, and a mixture thereof.

In the present invention, the solvent may be included in an amount up to 90 wt % relative to the total weight of the composition, regardless of its type.

Specifically, in the present invention, the solvent may be included in an amount of 10 wt % or more, 15 wt % or more, 25 wt % or more, 30 wt % or more, 35 wt % or more, or 40 wt % or more, or 90 wt % or less, 80 wt % or less, 70 wt % or less, 65 wt % or less, 60 wt % or less, or 55 wt % or less based on the total weight of the composition. More specifically, the solvent may be included in an amount of 30 to 70 wt %, 35 to 70 wt %, 35 to 65 wt %, 40 to 65 wt %, 35 to 60 wt %, 40 to 60 wt %, 35 to 55 wt %, or 40 to 55 wt %, based on the total weight of the composition, but is not limited thereto.

When the cosmetic composition of the present invention includes a non-aqueous solvent, a solvent other than water in the non-aqueous solvent may be included in an amount of 10 wt % or more, 15 wt % or more, 25 wt % or more, 30 wt % or more, or 40 wt % or more, or 80 wt % or less, 70 wt % or less, or 60 wt % or less, based on the total weight of the composition.

In the present invention, when water is used as a solvent in the composition, water may be included in an amount of 1 wt % or more, 10 wt % or more, 15 wt % or more, 20 wt % or more, or 25 wt % or more, or 80 wt % or less, 70 wt % or less, 60 wt % or less, or 55 wt % or less, based on the total weight of the composition.

Although vitamin C may be dissolved in water in a relatively large amount, there was a problem in that it was easily decomposed due to rapid oxidation. To improve oxidation stability, a non-aqueous solvent was used or vitamin C was stored at low temperatures, but solubility decreased when a non-aqueous solvent was used, and there was a risk of vitamin C precipitating when stored at low temperatures.

However, vitamin C is included in the form of a eutectic mixture with betaine as in the present invention, oxidation stability may be improved, it is possible to prevent precipitation at room temperature or low temperatures, and the skin permeability of vitamin C, which has difficulty in permeating the stratum corneum of the skin, may be improved.

In the present invention, "oxidation stability" means i) preventing vitamin C from being decomposed by light, heat, water, or other components in the composition, and specifically, preventing decomposition by water or heat. In particular, in the present invention, oxidation stability may mean that the concentration of vitamin C is maintained at, for example, 70% or more, 75% or more, 80% or more, 85% or more, 87% or more, 88% or more, 89% or more, or 90% or more, relative to the initial concentration, when vitamin C is stored at 30 to 60° C. for 4 weeks. More specifically, oxidation stability may mean that the concentration of vitamin C is maintained at 85% or more, 86% or more, 87% or more, 88% or more, 89% or more, 90% or more, 91% or more, 92% or more, 93% or more, 94% or more, 95% or more, 96% or more, relative to the initial concentration, when vitamin C is stored at 40 to 50° C. for 4 weeks.

In the present invention, "low-temperature precipitation" may mean that the dissolved component precipitates when stored at a low temperature for one week. The low temperature may be 10° C. or less, 8° C. or less, 6° C. or less, 4° C. or less, 2° C. or less, 0° C. or less, specifically 5° C. or less, 4° C. or less, 3° C. or less.

The prevent invention may provide a cosmetic composition, which comprises the eutectic mixture, for skin brightening, skin tone improvement, or pigmentation improvement.

The present invention may provide a cosmetic composition, which comprises the eutectic mixture, for improving skin wrinkles or elasticity.

In another aspect, the present invention provides a method for skin brightening, skin tone improvement, or pigmentation improvement, which comprises applying or administering the cosmetic composition comprising a eutectic mixture, which contains vitamin C and betaine, to the skin.

In another aspect, the present invention provides a method for skin wrinkle improvement or skin elasticity improvement, which comprises applying or administering the cosmetic composition comprising a eutectic mixture, which contains vitamin C and betaine, to the skin.

In another aspect, the present invention provides a use of a eutectic mixture comprising vitamin C and betaine, for the preparation of a cosmetic composition for skin brightening, skin tone improvement, or pigmentation improvement.

In another aspect, the present invention provides a use of a eutectic mixture comprising vitamin C and betaine, for the preparation of a cosmetic composition for skin wrinkle improvement or skin elasticity improvement.

The phrases "skin brightening," "skin tone improvement," and "pigmentation improvement" refer to all actions such as preventing the deposition of melanin pigment, suppressing the formation of freckles or blemishes, or evening out skin tone.

The phrase "skin wrinkle improvement" refers to suppressing the formation of wrinkles on the skin or alleviating the wrinkles that have formed on the skin, and the phrase "skin elasticity improvement" refers to reducing the degree of loose and sagging skin.

When vitamin C is included in the form of a eutectic mixture as in the present invention, not only the oxidation stability and skin permeability of vitamin C, but also cosmetic effects such as skin brightening, skin wrinkle improvement, or elasticity improvement may be improved.

The cosmetic composition of the present invention may further include all types of components, which can be used in commonly used cosmetics, such as moisturizers including glycerin, butylene glycol, propylene glycol, hexanediol, methylgluceth-20, diglycerin, and ethylhexylglycerin: sunscreen agents including ethylhexylmethoxycinnamate, ethylhexyl salicylate, ethylhexyltriazone, octocrylene, and bis-ethylhexyloxyphenolmethoxyphenyltriazine: pH adjusters including triethanolamine: thickeners including carbomer, xanthan gum, acrylate/C10-30 alkyl acrylate crosspolymer, and hyaluronic acid: preservatives including phenoxyethanol, methylparaben, and propylparaben: antioxidants including BHT, ethyl ascorbyl ether, and ascorbic acid: skin conditioning agents including beta-glucan; surfactants including cetearyl glucoside and sorbitan stearate; and fragrances or colorants, and there is no limitation to the components.

The cosmetic composition according to the present invention may be prepared in any formulation commonly prepared in the art. For example, the cosmetic composition may have a formulation such as a lotion such as a softening lotion or a nourishing lotion, a spray-type lotion, an emulsion including a facial lotion and a body lotion, a cream including a nutritional cream, a moisture cream and an eye cream, a stick, an essence, a cosmetic ointment, a spray, a gel, a face pack, a sunscreen, a makeup base, a liquid-type or spray-type foundation, powder, a makeup remover including a cleansing lotion and a cleansing oil, and a cleansing agent including a cleansing foam, soap and body wash, but is not limited thereto.

In one specific embodiment, the formulation of the cosmetic composition may be a balm, a water-in-oil (W/O) emulsion, an oil-in-water (O/W) emulsion, a solubilized formulation, or an oil formulation.

The present invention provides a method of preparing the cosmetic composition.

Specifically, the method comprises: preparing a eutectic mixture by mixing vitamin C and betaine; and preparing a cosmetic composition comprising the eutectic mixture.

The step of preparing the eutectic mixture may comprise additionally adding water.

In the preparation method, for the vitamin C, betaine, water, eutectic mixture, and cosmetic composition, the content described above may be applied as is.

The step of preparing the eutectic mixture may comprise: mixing vitamin C and betaine; and stirring the mixture at a speed of 100 to 5000 rpm at a temperature from 45 to 95° C.

The stirring step may be stirring the mixture until the components constituting the eutectic mixture become homogeneous. More preferably, it may be stirring the mixture for additional 0.5 to 2 minutes after confirming the homogeneity of the eutectic mixture.

In addition, a method of confirming the homogeneity of the eutectic mixture may comprise:

i) a method of checking whether a transparent mixture is formed without precipitation when a eutectic mixture, which is a super-melted solution dissolved beyond the solubility of each component, is illuminated with light in front of a black background, and ii) a method of checking the melting point using a differential scanning calorimetry (DSC) device because a single melting point is attained at a temperature lower than the melting point of each component when a eutectic mixture is formed.

The step of preparing the cosmetic composition may comprise mixing with a component for preparing a cosmetic formulation. The component is not limited as long as it is commonly added to cosmetic formulations.

The present invention provides a quasi-drug composition comprising a eutectic mixture, which contains vitamin C and betaine.

In the quasi-drug composition according to the present invention, for the vitamin C, betaine, and eutectic mixture, the content described above for the cosmetic composition may be applied as is.

The present invention may provide a quasi-drug composition, which comprises the eutectic mixture, for skin brightening, skin tone improvement, or pigmentation improvement.

The present invention may provide a quasi-drug composition, which comprises the eutectic mixture, for skin wrinkle improvement or elasticity improvement.

In another aspect, the present invention provides a method for skin brightening, skin tone improvement, or pigmentation improvement, which comprises applying or administering the quasi-drug composition comprising a eutectic mixture, which contains vitamin C and betaine, to the skin.

In another aspect, the present invention provides a method for skin wrinkle improvement or skin elasticity improvement, which comprises applying or administering the quasi-drug composition comprising a eutectic mixture, which contains vitamin C and betaine, to the skin.

In another aspect, the present invention provides a use of a eutectic mixture comprising vitamin C and betaine, for the preparation of a quasi-drug composition for skin brightening, skin tone improvement, or pigmentation improvement.

In another aspect, the present invention provides a use of a eutectic mixture comprising vitamin C and betaine, for the preparation of a quasi-drug composition for skin wrinkle improvement or skin elasticity improvement.

The present invention provides a method of preparing the quasi-drug composition.

Specifically, the method comprises: preparing a eutectic mixture by mixing vitamin C and betaine; and preparing a quasi-drug composition comprising the eutectic mixture.

In the method of preparing the quasi-drug composition, for the vitamin C, betaine, water, eutectic mixture, and quasi-drug composition, the content described above may be applied as is.

Each of the above-mentioned components included in the cosmetic composition and the quasi-drug composition according to the present invention may be preferably used in the cosmetic composition and the quasi-drug composition of the present invention within a range not exceeding the maximum usage specified in the regulations related to <Cosmetics Use and Permission> by governments around the world.

Hereinafter, the present invention will be described in detail through experimental examples below. The following experimental examples only illustrate the present invention, and the content of the present invention is not limited by the following experimental examples. In addition, the experimental examples are only for the purpose of helping understanding of the present invention, and the scope of the present invention is not limited by them in any way.

EXAMPLES

Experimental Example 1. Confirmation of Stability of Eutectic Mixture Comprising Vitamin C at Room Temperature and Low Temperature Ascorbic acid and betaine were prepared as components of the eutectic mixture according to the molar ratios in Tables 1 and 2, and water was added so that the content of water was 14 wt % based on the total weight of the eutectic mixture. The components shown in Tables 1 and 2 were stirred at 80° C. and 500 rpm for 5 minutes, and after confirming the formation of a liquid eutectic mixture, heating was stopped and the mixture was naturally cooled.

In order to evaluate the stability of the eutectic mixture, the eutectic mixture prepared above was stored at room temperature and low temperature (4° C.) for 1 week to check whether the form of the eutectic mixture remained stable without precipitation. The results of comparing the stability depending on the molar ratio of ascorbic acid and betaine are shown in Tables 1 and 2 below and FIG. 1.

[Eutectic Mixture Stability Evaluation Criteria]

X: No precipitation

O: Precipitation occurs

TABLE 1

| (Parts by weight) | Preparation Example 1 | Preparation Example 2 | Preparation Example 3 | Preparation Example 4 | Preparation Example 5 | Preparation Example 6 |
|---|---|---|---|---|---|---|
| Molar ratio of ascorbic acid:betaine | 2.5:1 | 2:1 | 1:1 | 1:2 | 1:4 | 1:5 |
| Ascorbic acid | 64.0 | 60.8 | 51.6 | 36.9 | 23.5 | 19.9 |
| Betaine | 17.0 | 20.2 | 34.4 | 49.1 | 62.5 | 66.1 |
| Potassium hydroxide | 5.0 | 5.0 | 0.0 | 0.0 | 0.0 | 0.0 |
| water | 14.0 | 14.0 | 14.0 | 14.0 | 14.0 | 14.0 |
| Total | 100 | 100 | 100 | 100 | 100 | 100 |
| Precipitation at room temperature | X | X | X | X | X | X |

TABLE 2

| (Parts by weight) | Preparation Example 2 | Preparation Example 3 | Preparation Example 4 | Preparation Example 5 |
|---|---|---|---|---|
| Molar ratio of ascorbic acid: betaine | 2:1 | 1:1 | 1:2 | 1:4 |
| Ascorbic acid | 60.8 | 51.6 | 36.9 | 23.5 |
| Betaine | 20.2 | 34.4 | 49.1 | 62.5 |
| Potassium hydroxide | 5.0 | 0.0 | 0.0 | 0.0 |
| water | 14.0 | 14.0 | 14.0 | 14.0 |
| Total | 100 | 100 | 100 | 100 |
| Precipitation at low temperature (4 °C) | X | X | X | X |

As shown in Tables 1 and 2, the eutectic mixtures of ascorbic acid and betaine were stable without precipitation even when stored at room temperature for 1 week, and it can be seen that they are stable at low temperatures because precipitation did not occur even when stored at 4° C. for 1 week.

Experimental Example 2. Evaluation of Stability of Composition Comprising Eutectic Mixture Comprising Vitamin C Compositions of Examples and Comparative Examples were prepared according to the compositions and contents shown in Table 3 below.

Each composition of Examples was prepared by forming the eutectic mixture of Preparation Example 2 according to Experimental Example 1 above, adding all the remaining components shown in Table 3 to it, stirring it for an additional 5 minutes, and cooling it naturally. Each composition of Comparative Examples was prepared by adding all the components shown in Table 3 below, stirring it for 5 minutes, and cooling it naturally.

The stability of the composition was evaluated in the same manner as in Experimental Example 1 above. Specifically, it was checked whether precipitation occurred when the compositions of Examples and Comparative Examples prepared above were stored at 4° C. for 1 week.

TABLE 3

| (Parts by weight) | Example 1 | Example 2 | Example 3 | Example 4 | Comparative Example 1 | Comparative Example 2 |
|---|---|---|---|---|---|---|
| Eutectic mixture of Preparation Example 2 | 49.3 | 49.3 | 49.3 | 49.3 | — | — |
| Ascorbic acid | — | — | — | — | 30.0 | 30.0 |
| Betaine | — | — | — | — | — | 10.0 |
| Propanediol | 30.35 | — | — | — | — | — |
| Butylene glycol | 0.50 | 30.85 | 0.50 | 0.50 | 0.50 | 0.50 |
| Dipropylene glycol | — | — | 30.35 | — | — | — |
| Glycerin | — | — | — | 30.35 | 30.35 | 30.35 |
| water | 17.2 | 17.2 | 17.2 | 17.2 | 34.0 | 24.0 |
| Ethanol | 2.65 | 2.65 | 2.65 | 2.65 | 2.65 | 2.65 |
| Potassium hydroxide | — | — | — | — | 2.5 | 2.5 |
| Total | 100 | 100 | 100 | 100 | 100 | 100 |
| Precipitation at low temperature (4 °C) | X | X | X | X | ○ | ○ |

As shown in Table 3, in Comparative Example 1 including only ascorbic acid and Comparative Example 2, in which ascorbic acid and betaine were simply mixed rather than in the form of a eutectic mixture, vitamin C was not stably dissolved because it precipitated at a low temperature.

However, it can be seen that in Examples 1 to 4, which included vitamin C and betaine in the form of a eutectic mixture, vitamin C was stably dissolved without precipitation at a low temperature.

Conventionally, vitamin C has low solubility in compositions including a large amount of polyol as a solvent, which causes precipitation when stored at low temperatures. However, when vitamin C is included in the form of a eutectic mixture, vitamin C was stably dissolved without precipitation at a low temperature even in compositions including polyol (such as propanediol, butylene glycol, dipropylene glycol, or glycerin) as seen in Examples 1 to 4.

Experimental Example 3. Confirmation of Skin Permeability

In order to confirm the skin permeability improving effect of the eutectic mixture, compositions of Examples, which included vitamin C in the form of a eutectic mixture, and compositions of Comparative Examples, which included vitamin C in the form of a simple mixture, were prepared.

In order to set the vitamin C content in the simple mixture and the eutectic mixture to be the same, an appropriate amount of the eutectic mixture was added after calculating the concentration of vitamin C in the eutectic mixture. The eutectic mixture of Preparation Example 3 prepared in Experimental Example 1 was used and mixed with the components according to the composition shown in Table 4 below and stirred at room temperature (25° C.) and 500 rpm for 5 minutes.

The skin permeability of the compositions of Examples and Comparative Examples prepared above was confirmed by the method below.

<Measurement of Skin Permeability>

Pig skin (area: 2.5 cm×2.5 cm, thickness: 1 mm, APURES Co., Ltd.) consisting of keratin, the epidermis, and part of the dermis was placed in a Franz cell whose receptor was filled with 2.5 mL of phosphate-buffered saline (PBS, pH 7.4, GIBCO). 100 μL of each composition was prepared, applied to a uniform area of pig skin and left for 8 hours at a temperature of 37° C. and 50% humidity. Afterward, the unabsorbed solution was removed, and the amount of vitamin C permeated into the skin and receptor was analyzed. To quantify the amount of vitamin C absorbed into the stratum corneum, a stripping tape for collecting keratin (D-Squame from CuDerm Corporation) was attached to the surface of pig skin and pressed for 10 seconds using a D-Squame pressure applicator (CuDerm), removed, and placed in a 1.5 mL tube. This process was repeated two more times on the same area of the skin. To elute vitamin C absorbed into the collected keratin, I mL of PBS solution was added to each tube. The remaining pig skin (epidermis and part of the dermis) was cut into small pieces, put into the PBS solution (1 mL), and homogenized using a tissue grinder to elute vitamin C absorbed into the skin. To measure the amount of vitamin C that permeated into the keratin, epidermis, dermis, and receptor, Megazyme's Ascorbic Acid Assay Kit (K-ASCO) was used. It is based on the principle that as L-ascorbic acid reduces 3-(4,5-dimethylthiazolyl-2)-2,5-diphenyltetrazolium bromide (MTT) to form MTT-formazan, the absorbance at the wavelength of 578 nm increases quantitatively in proportion to the amount of L-ascorbic acid. Therefore, the amount of vitamin C permeated into the skin was obtained by adding up the amount of vitamin C measured in the keratin, epidermis, dermis, and receptor.

TABLE 4

| (Parts by weight) | Example 5 | Example 6 | Example 7 | Comparative Example 3 | Comparative Example 4 |
|---|---|---|---|---|---|
| Eutectic mixture of Preparation Example 3 | 48.4 | 48.4 | 48.4 | — | — |
| Ascorbic acid | — | — | — | 25 | 25 |
| water | 51.6 | 1.3 | 1.3 | 75 | — |
| Propanediol | — | 50.3 | — | — | 75 |
| Glycerin | — | — | 50.3 | — | — |
| Total | 100 | 100 | 100 | 100 | 100 |
| Permeation amount (μg) | 1138 | 680 | 953 | 626 | 376 |

As shown in Table 4, it can be seen that based on the same content of vitamin C, the amount of vitamin C permeated into the skin in Examples 5 to 7, which included vitamin C in the form of a eutectic mixture, was greater than that of vitamin C permeated into the skin in Comparative Examples 3 and 4, in which vitamin C was simply mixed.

Meanwhile, the compositions of Example 8 and Comparative Examples 5 and 6 were prepared according to the components shown in Table 5 below in the same manner as in Examples 5 to 7 and Comparative Examples 3 and 4, and their skin permeability was confirmed.

Here, the eutectic mixture of Preparation Example 2 prepared in Experimental Example 1 was used, and the composition of Example 8 was prepared by adding it to glycerin and stirring it at room temperature. The compositions of Comparative Examples 5 and 6 were prepared by adding the components according to the compositions shown in Table 5 below to glycerin and stirring the same at room temperature (25° C.) and 500 rpm for 5 minutes.

TABLE 5

| (Parts by weight) | Example 8 | Comparative Example 5 | Comparative Example 6 |
|---|---|---|---|
| Eutectic mixture of Preparation Example 2 | 49.3 | — | — |
| Ascorbic acid | — | 30.0 | 30.0 |
| Betaine | — | 10.0 | — |
| water | 0.1 | 6.9 | 6.9 |
| Glycerin | 50.6 | 50.6 | 50.6 |
| Potassium hydroxide | — | 2.5 | 2.5 |
| Total | 100 | 100 | 90 |
| Permeation amount (μg) | 351 | 163 | 103 |

As shown in Table 5, it can be seen that the amount of vitamin C permeated into the skin in Example 8, which included the eutectic mixture of Preparation Example 2, was greater than that in Comparative Examples 5 and 6, in which vitamin C was simply mixed.

Accordingly, it can be seen that simply using vitamin C together with betaine (Comparative Example 5) does not achieve the same effect as preparing a eutectic mixture comprising vitamin C and that the amount of vitamin C permeated into the skin increases by comprising vitamin C in the form of a eutectic mixture.

Experimental Example 4. Evaluation of Vitamin C Titer Maintenance

A cosmetic composition comprising a high concentration of a eutectic mixture comprising vitamin C and a cosmetic composition comprising a high concentration of vitamin C were prepared according to the compositions shown in Table 6 below. Specifically, the composition of Example 9 was prepared by mixing the eutectic mixture of Preparation Example 3 prepared in Experimental Example 1 with the components shown in Table 6 below. The composition of Comparative Example 7, which is a non-aqueous composition, was prepared in the form of simple vitamin C without water. For the prepared Example and Comparative Example compositions, the stability of vitamin C at a high temperature was compared.

TABLE 6

| Materials (parts by weight) | Example 9 | Comparative Example 7 |
|---|---|---|
| Eutectic mixture of Preparation Example 3 | 50.4 | — |
| Ascorbic acid | — | 26 |
| water | 26.5 | — |
| Propanediol | 5 | 72.7 |
| Glycerin | 3 | — |
| PEG-75 | 0.5 | — |
| Butylene glycol | 4 | — |
| Dipropylene glycol | 4 | — |
| Ethanol | 4 | — |
| Dexpanthenol | 1 | — |
| Triisostearin | 0.5 | — |
| 1,2-hexanediol | 1 | — |
| Sodium metabisulfite | 0.1 | — |
| Potassium hydroxide | — | 1.3 |
| Total | 100 | 100 |

In order to confirm the high-temperature stability of vitamin C in a cosmetic composition comprising vitamin C in the form of a eutectic mixture, the compositions of Example 9 and Comparative Example 7 were stored at 40° C. and 50° C. for 4 weeks to confirm the titer of vitamin C, and the results thereof are shown in Table 7.

TABLE 7

| Storage temperature | Example 9 | Comparative Example 7 |
|---|---|---|
| 40 °C | 93.3% | 87.1% |
| 50 °C | 90.1% | 69.2% |

As shown in Table 7, it can be seen that despite the composition containing a large amount of water in which vitamin C is easily oxidized, the composition of Example 9, which comprised vitamin C in the form of a eutectic mixture, was not decomposed and maintained more stably in the composition compared to the non-aqueous composition of Comparative Example 7.

Experimental Example 5. Confirmation of Structure of Vitamin C-Betaine Eutectic Mixture In this experiment, to confirm the specific structure of the eutectic mixture of Preparation Example 2 in Table 1, infrared spectroscopy and NMR spectroscopy were performed.

1) Infrared Spectrum Analysis

The formation and interaction of the ascorbic acid-betaine eutectic mixture may be confirmed using infrared spectroscopy. It is known that the formation of a eutectic mixture depends on hydrogen bonding, and in infrared spectroscopy, the hydrogen bonding can be explained by changes in the bond length and vibrations corresponding to hydrogen bonding. For comparison with the eutectic mixture, a simple mixture (physical mixture) with the same composition as the eutectic mixture was also measured. The physical mixture was prepared by stirring materials with the same composition as the ascorbic acid-betaine eutectic mixture (molar ratio of 2:1) in Table 1 at room temperature (25° C.) and 500 rpm for 5 minutes until uniformly mixed. In addition, the infrared spectra of ascorbic acid and betaine aqueous solutions were measured and compared as reference data. First, in the infrared spectrum of FIG. 3A, bands corresponding to the characteristic stretching vibrations of C═C and C═O of ascorbic acid appeared at 1679 $cm^{-1}$ and 1758 $cm^{-1}$, respectively. On the other hand, in the infrared spectrum of betaine, bands corresponding to the characteristic stretching vibrations of the carboxylate group ($COO^-$) and C—N appeared at 1621 $cm^{-1}$ and 1399 $cm^{-1}$, respectively. FIGS. 3A and 3B show the infrared spectra of the eutectic mixture and the physical mixture measured in the wavenumber ranges of 1000 to 2000 $cm^{-1}$ and 2000 to 4000 $cm^{-1}$. Each of the spectra of the physical mixture and the eutectic mixture had a form of overlapping the spectra of ascorbic acid and betaine, but the movement of several vibration bands were confirmed in the eutectic mixture compared to the physical mixture. As shown in FIG. 3A, the $COO^-$ vibration band of betaine is red shifted from 1623 $cm^{-1}$ (in physical mixture) to 1603 $cm^{-1}$. This red shift means that the intramolecular bond length has increased and a physical bond has been formed between ascorbic acid and betaine. In addition, in FIG. 3B, the sharp O—H stretching vibration peaks (3212, 3311, 3406, 3523 $cm^{-1}$) of ascorbic acid in the physical mixture appeared as one band (3260-3356 $cm^{-1}$) with a very wide peak width. This wider band shows that many hydrogen bonds were formed between pure ascorbic acid and betaine when the eutectic mixture was formed.

2) NMR Analysis

To further confirm the interaction between ascorbic acid and betaine, $^1H$ nuclear magnetic resonance spectroscopy (NMR) was performed on ascorbic acid, betaine, and the ascorbic acid-betaine eutectic mixture.

Figure 4B:
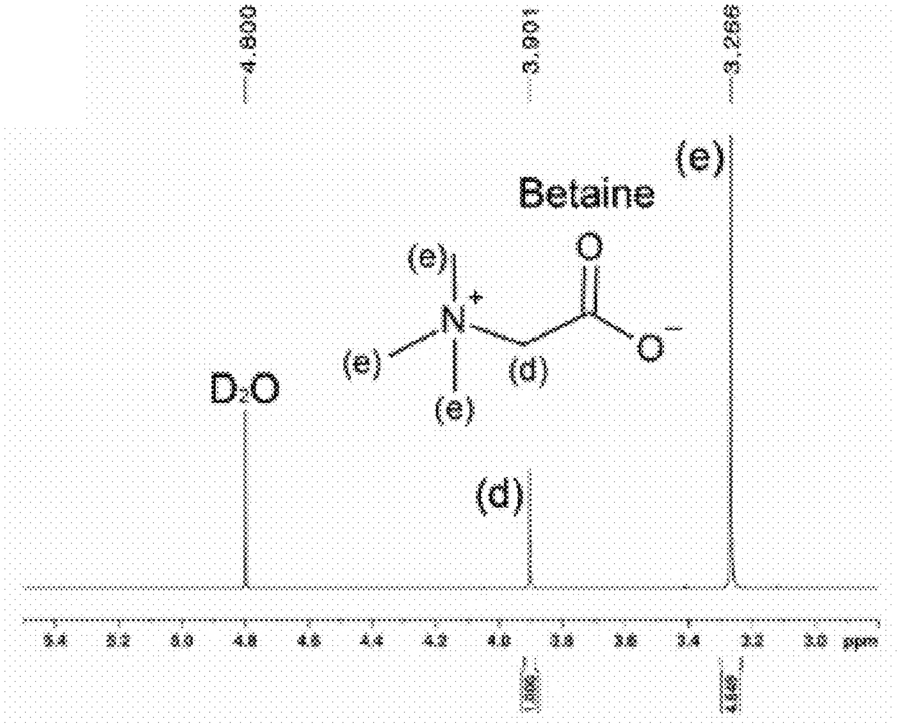
FIG. 4B shows the $^{1}H$ NMR analysis result of betaine, according to Experimental Example 5.

As shown in FIG. 4, even when a eutectic mixture is formed, chemical shifts corresponding to ascorbic acid and betaine are still present, which suggests that only physical interactions are involved without any chemical reaction when the eutectic mixture is formed. The electron density of the protons present in ascorbic acid and betaine changed due to the hydrogen bond formed between the components of the eutectic mixture, and thus chemical shifts occurred.

In particular, in the case of the proton peak (4.958-4.955 ppm) connected to 4C in the lactone ring structure of ascorbic acid, an upfield shift appeared. As shown in FIG. 5, a larger shift was observed as the proportion of ascorbic acid increased (here, the molar ratios of ascorbic acid:betaine were 1:1, 1.5:1, and 2:1 in FIGS. 5A to 5C respectively, and a shift to 4.894-4.890 ppm occurred at the 1:1 molar ratio of ascorbic acid:betaine, a shift to 4.857-4.854 ppm occurred at the 1.5:1 molar ratio, and a shift to 4.812-4.808 ppm occurred at the 2:1 molar ratio). These upfield shifts indicate that the electron density around the proton has increased due to intermolecular interactions, which may prove the formation of a hydrogen bond between ascorbic acid and betaine.

Experimental Example 6: Evaluation of Skin Brightening, Skin Tone Uniformity, Wrinkle Improvement, and Elasticity Improvement Ten female subjects in their 20s and 30s were asked to apply an ampoule (23% vitamin C) comprising the eutectic mixture of Preparation Example 2 prepared in Experimental Example 1 to the skin of the entire face once every evening for 4 weeks, and skin brightness, skin tone uniformity, skin wrinkles, and skin elasticity were measured for 4 weeks to confirm the skin improvement effect. The compositions and their content of the ampoule are shown in Table 8 below.

TABLE 8

| (Parts by weight) | Ampoule formulation example |
|---|---|
| Eutectic mixture of Preparation Example 2 | 37.80 |
| water | 18.40 |
| Propanediol | 26.40 |
| Dipropylene glycol | 10.50 |
| Glycerin | 3.00 |
| Dexpanthenol | 1.50 |
| Disodium EDTA | 0.05 |
| 1,2-Hexanediol | 1.50 |
| Sodium metabisulfite | 0.20 |
| Xanthan gum | 0.15 |
| Potassium hydroxide | 0.50 |
| Total | 100.00 |

All measurements were performed after adaptation of subjects' skin in a constant temperature and constant humidity environment for 20 minutes to achieve the same skin conditions.

Skin brightness was measured using a Chroma Meter CR-400 device to measure the L value, which is the brightness of the same area of the face, before using the ampoule (0 weeks) and 2 and 4 weeks after using the ampoule.

Skin tone uniformity and skin wrinkles were measured using Antera 3D® CS (from Miravex). Skin tone uniformity was measured 2 and 4 weeks after using the ampoule on the same cheek area, and the skin tone uniformity improvement rate was obtained by calculating the increase in uniformity after using the ampoule relative to the uniformity before using the ampoule.

The wrinkle improvement rate was obtained by calculating the decrease in the wrinkle indentation index at 2 and 4 weeks after using the ampoule compared to the 0-week indentation index measured by Antera 3D of the nasolabial fold area. Skin elasticity (R5, net elasticity) was measured before starting the experiment and 2 and 4 weeks after using the ampoule on the same cheek area, using a Cutometer® MPA580 device (from Courage and Khazaka Electronic GmbH). The skin elasticity improvement rate was obtained by calculating the increase in the R5 value after using the ampoule relative to the R5 value before using the ampoule. The measurement results are shown in FIGS. 6 and 7, respectively.

As shown in FIGS. 6 and 7, it can be seen that when applied to the skin, the eutectic mixture comprising vitamin C has an effect of improving skin brightening, skin tone uniformity, skin wrinkles and skin elasticity.

The invention claimed is:

1. A cosmetic composition comprising a eutectic mixture comprising (i) a binary structure consisting of vitamin C and betaine in a hydrogen-bonding network, and (ii) at least one cosmetic component, wherein the vitamin C and the betaine are included in the eutectic mixture in a molar ratio of 2:1 to 1:1; and wherein the eutectic mixture is included in an amount of 0.00001 to 80 parts by weight based on 100 parts by total weight of the cosmetic composition.

2. The cosmetic composition of claim 1, wherein the vitamin C is included in an amount of 6 parts by weight to 94 parts by weight based on 100 parts by weight of the total eutectic mixture.

3. The cosmetic composition of claim 1, wherein the eutectic mixture further comprises (iii) water.

4. The cosmetic composition of claim 1, wherein the cosmetic composition further comprises an aqueous solvent, a non-aqueous solvent, or a mixture thereof.

5. A method for treatment of skin, comprising applying an effective amount of the cosmetic composition of claim 1 to a subject in need thereof, wherein the treatment of skin is for skin brightening, skin tone improvement, or pigmentation improvement.

6. The method of claim 5, wherein the treatment of skin is for improving skin wrinkles or skin elasticity.

7. A method of preparing a cosmetic composition, comprising:

preparing a eutectic mixture comprising a binary structure consisting of vitamin C and betaine in a hydrogen-bonding network by mixing the vitamin C and the betaine; and adding the eutectic mixture to at least one cosmetic component to prepare the cosmetic composition, wherein the vitamin C and the betaine are included in the eutectic mixture in a molar ratio of 2:1 to 1:1; and wherein the eutectic mixture is included in an amount of 0.00001 to 80 parts by weight based on 100 parts by total weight of the cosmetic composition.

8. The method of claim 7, wherein the step of preparing the eutectic mixture includes additionally adding water.

* * * * *